(12) United States Patent
Fovet et al.

(10) Patent No.: US 9,181,575 B2
(45) Date of Patent: *Nov. 10, 2015

(54) DETECTION AND ENUMERATION OF MICROORGANISMS

(75) Inventors: Yannick Fovet, Ludwigshafen (DE); Sam Dukan, Marseilles (FR); Adrien Ducret, Marseilles (FR)

(73) Assignees: BASF SE, Ludwigshafen (DE); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 767 days.

This patent is subject to a terminal disclaimer.

(21) Appl. No.: 12/934,834

(22) PCT Filed: Mar. 20, 2009

(86) PCT No.: PCT/EP2009/053295
§ 371 (c)(1),
(2), (4) Date: Nov. 30, 2010

(87) PCT Pub. No.: WO2009/121726
PCT Pub. Date: Oct. 8, 2009

(65) Prior Publication Data
US 2011/0065145 A1 Mar. 17, 2011

(30) Foreign Application Priority Data

Apr. 4, 2008 (GB) .................................. 0806135.0
Jan. 20, 2009 (GB) .................................. 0900850.9

(51) Int. Cl.
*C12Q 1/06* (2006.01)
(52) U.S. Cl.
CPC ............ *C12Q 1/06* (2013.01); *G01N 2333/195* (2013.01)
(58) Field of Classification Search
None
See application file for complete search history.

(56) References Cited

U.S. PATENT DOCUMENTS

2005/0202518 A1* 9/2005 Vedrine et al. ............... 435/7.32
2007/0218522 A1 9/2007 McCoy

FOREIGN PATENT DOCUMENTS

EP 1 329 515 A 7/2003

OTHER PUBLICATIONS

Tesh et al. Journal of Clinical Microbiology, Jun. 1983, vol. 154, No. 3 pp. 1104-1109.*
Ray et al., Applied Microbiology, vol. 25, No. 4, Apr. 1973, pp. 499-503.
Dutil S et al. Detection of *Legionella* spp. By fluorescent in situ hybridization in dental unit waterlines. J Appl Microbiol. May 2006; 100(5):955-63*.
Diederen et al. Evaluation of real-time PCR for the early detection of *Legionella pneumophila* DNA in serum samples. J Med Microbiol. Jan. 2007; 56 (pt1):94-101*.
Speck et al, Repair and enumeration of injured coliforms by a plating procedure, Appl Microbiol 29, 549-50 (1975).
Martin et al, Catalase: its effect on microbial enumeration. Appl Environ Microbiol 32, 731-4 (1976).
Brewer et al, Beneficial effects of catalase or pyruvate in a most-probable-number technique for the detection of *Staphylococcus aureus*. Appl Environ Microbiol 34, 797-800 (1977).
McDonald et al, Enhanced recovery of injured *Escherichia coli* by compounds that degrade hydrogen peroxide or block its formation. Appl Environ Microbiol 45, 360-5 (1983).
Marthi et al. Resuscitation effects of catalase on airborne bacteria. Appl Environ Microbiol 57, 2775-6 (1991).
Busch and Donnelly. Development of a repair-enrichment broth for resuscitation of heat-injured *Listeria monocytogenes* and *Listeria innocua*. Appl Environ Microbiol 58, 14-20 (1992).
Dukan et al, Oxidative stress defense and deterioration of growth-arrested *Escherichia coli* cells. J Biol Chem 274, 26027-32 (1999).
Bang et al, Recovery and detection of *Vibrio vulnificus* during cold storage. Food Microbiol 24, 664-70, (2007)*.
Bissonnette et al, Evaluation of recovery methods to detect coliforms in water. Appl Environ Microbiol 33, 590-595, (1977).
Budu-Amoako et al. Evaluation of the ability of primary selective enrichment to resuscitate heat-injured and freeze injured *Listeria monocytogenes* cells. Appl Environ Microbiol 58, 3177-9 (1992).
Martin et al, Rapid determination of *Listeria monocytogenes* in foods using a resuscitation/selection/kit system detection. J AOAC Int 76, 632-6 (1993).
Pine et al, Development of a chemically defined liquid medium for growth of *Legionella pneumophila*. J Clin Microbiol 9, 615-26 (1979).
Teo et al, Development of a simple recovery-enrichment system for enhanced detection of heat-injured *Listeria monocytogenes* in pasteurized milk. J Food Prot 63, 462-72 (2000).
Teo et al, Optimizing detection of heat-injured *Listeria monocytogenes* in pasteurized milk. J Food Prot 64, 1000-11. (2001).
Ewann et al, Cysteine Metabolism in *Legionella pneumophila*: Charac Cystine-Utilizing Mutant. Appl Environ Microbiol, Jun. 2006, 72(6), 3993-4000*.
LeBlanc et al, Compensatory Functions of Two Alkyl Hydroperoxide Reductases in the Oxidative Defense System of *Legionella pneumophila*. Journal of Bacteriology, Sep. 2006, vol. 188, No. 17, 6235-6244*.

(Continued)

*Primary Examiner* — Vera Afremova
(74) *Attorney, Agent, or Firm* — Shruti Costales (57) ABSTRACT

A method for detecting and enumerating viable microorganisms in a sample suspected of containing said microorganisms (1) contacting said microorganisms of said sample with at least one repair compound and a growth medium, and (2) incubating the product of steps (1), and (3) detecting and quantifying said viable microorganisms, in which the microorganisms are of the species *Legionella pneumophila*, and in which the repair compound directly or indirectly causes an effect on the metabolism to reduce the oxidative stress of the microorganism. The invention also includes a kit for more accurately detecting and enumerating viable microorganisms of the species *Legionella pneumophila* in a sample suspected of containing said microorganisms.

6 Claims, 5 Drawing Sheets

(56) References Cited

OTHER PUBLICATIONS

Transactions of the Royal Society of Tropical Medicine and Hygiene, vol. 88, No. 1, Jan. 1994, pp. 19-26.
Arata et al, Life Sciences, vol. 49, No. 6, Jan. 1991, pp. 473-479.
Baker et al, Biochemical and Biophysical Research Communications, vol. 320, No. 3, Jul. 2004. pp. 833-839.
Delgado-Viscogliosi Pilar et al, Applied and Environmental Microbiology, vol. 71, No. 7, Jul. 2005. pp. 4086-4096.
Pine et al, Journal of Clinical Microbiology, vol. 23, 1986, pp. 33-42.
Berube et al., Applied and Environmental Microbiology, 1989, vol. 55, pp. 1640-1641.
Calabrese, Joseph P., & Bissonnette, Gary K. "Improved detection of acid mine water stressed coliform bacteria on media containing catalase and sodium pyruvate", Canadian Journal of Microbiology, Mar. 2, 1990, vol. 36, pp. 544-550.
Strickhouser, Amanda Ellen, "*Legionella pneumophila* in Domestic Hot Water Systems: Evaluation of Detection Methods and Environmental Factors Affecting Survival", Thesis submitted to the Virginia Polytechnic Institute & State University, Blacksburg, VA, Nov. 26, 2007, pp. 1-86, available online at http://scholar.lib.vt.edu/theses/available/etd-12102007-140222/unrestricted/StrickhouserThesis.pdf.
Biokar Diagnostics, Confirmation Agars for *Legionella* (BCYE-alpha and BCYE-alpha without Cysteine), Feb. 16, 2009, pp. 1-4, available online at http://www.solabia.fr/solabia/produitsDiagnostic.nsf/0/C17A5F63CA187697C12574C900330BC8/$file/TDS__BT007_v3.pdf.
Biokar Diagnostics, GVPC Agar for *Legionella*, Feb. 17, 2009, pp. 1-5, available online at http://www.solabia.fr/solabia/produitsDiagnostic.nsf/0/C17A5F63CA187697C12574C900330BC8/$file/TDS__BM071_v4.pdf.
Hardy Diagnostics, Buffered Charcoal Yeast Extract (BCYE) Agar, accessed Jul. 1, 2013, pp. 1-10, available online at https://catalog.hardydiagnostics.com/cp_prod/Content/hugo/BCYEAgar.htm.
Standard Method T 90-431 (ISSN 0335-3931), edited and distributed by the French Association of Normalization (AFNOR), 11 Avenue Francis de Pressense—93571 St Denis La Plaine Cedex, France, Apr. 2006, pp. 1-52.
Pine, L. et al., "Guanine is a Growth Factor for *Legionella* Species", Journal of Clinical Microbiology, Jan. 1986, vol. 23, No. 1, pp. 163-169.

\* cited by examiner

DETECTION AND ENUMERATION OF MICROORGANISMS

FIELD OF THE INVENTION

The present invention concerns a method for detecting and enumerating viable microorganisms of the species *Legionella pneumophila* in a sample. The invention also includes a kit suitable for use in such a method. This method and kit enable viable microorganisms to be quantified more rapidly.

BACKGROUND OF THE INVENTION

*Legionella* bacteria are ubiquitous in wet or moist environments such as soil and non-marine aquatic habitats. They can also be found in warm and cold water installations, cooling towers of air conditioning systems and water humidifiers.

*Legionella*, especially *Legionella pneumophila*, are pathogens that can cause an acute bacterial pneumonia, generally known as "legionnaires disease", which is often lethal for infected individuals.

Traditionally detection and enumeration of *Legionella pneumophila* are achieved by cell culturing. This method may be achieved by measuring culturable bacteria using plate count or measuring micro-colonies employing a filter membrane method. These techniques evaluate viable bacteria by their ability to form a colony or micro-colony. Unfortunately, such methods usually require between 3 and 10 days in order to allow the colonies or micro-colonies to form. Where water installations are still in operation there is an unacceptable risk of human infection during this time.

Other methods for detecting total *Legionella* microorganisms include PCR (Polymerase Chain Reaction) techniques. PCR employs DNA polymerase to amplify a piece of DNA by in vitro enzymatic replication. During the progression of the technique the DNA generated is used as a template for replication which brings about a chain reaction in which the DNA template is exponentially amplified. PCR enables a single or few copies of a piece of DNA to be amplified by generating millions or more copies of the DNA piece. Typically such a method is described by Diederen et al., J Med. Microbiol. 2007 January; 56 (Pt 1):94-101.

However a drawback of PCR is that the samples tend to contain polymerisation reaction inhibitors and therefore do not consistently provide quantitative results. Furthermore, the technique relies upon a prior DNA purification step which can result in loss of DNA with the consequential underestimation of the *Legionella* present. To some extent these disadvantages are overcome by real-time PCR which is quantitative. However, the technique cannot distinguish between viable cells and non-viable cells.

Another technique is fluorescent in situ hybridisation (FISH) in which an oligonucleotidic probe labelled by a fluorescent substance penetrates into the bacteria cells. Where the ribosomal nucleic acids (rRNA) have the correct sequence to the probe known as the target, the probe will attach itself to its target and will not be removed by any subsequent washing step. The bacteria in which the probe is fixed will then emit a fluorescent signal. This fluorescent signal may then be quantified by techniques such as flow cytometry, solid phase cytometry, or epifluorescent microscopy. A typical FISH technique is described by Dutil S et al J Appl Microbiol. 2006 May; 100(5):955-63. However, using the FISH technique alone the total number of viable *Legionella pneumophila* could be detected but unfortunately the method could not exclusively identify only those *Legionella pneumophila* bacteria able to divide and by consequence make a colony.

A further method for enumerating viable *Legionella pneumophila* involves ChemChrome V6 and is described by Delgado-Viscogliosi et al Appl Environ Microbiol. 2005 July; 71(7):4086-96. This method allows the quantification of *Legionella pneumophila* as well as discrimination between viable and non-viable bacteria. It combines specific detection of *Legionella* cells using antibodies and a bacterial viability marker (ChemChrome V6) and employing epifluorescent microscopy for the enumeration. However, although this technique distinguishes between viable and non-viable cells it is not able to separately identify those colony-forming bacteria.

US 20070218522 describes methods and compositions for detecting and quantifying viable *Legionella* and other heterotrophic aerobic bacteria the method includes the use of dipslides that include an absorbent medium, growth promoting and growth selective substances for rapid detection and quantification of micro-colonies of *Legionella*. This technique would not enumerates injured bacteria.

EP 1329515 relates to a method of testing for the presence of microorganisms in a gaseous environment comprising hydrogen peroxide by bringing the gaseous environment into contact with an agar growth medium comprising a salt of pyruvic acid and allowing the development of colonies of the microorganisms.

Techniques which involve the growth of colonies on a growth medium, such as a nutrient agar plate, are generally considered to be more accurate. Consequently the plate count method remains the preferred choice of method for obtaining the total viable count. This generally means applying a sample suspected of containing the microorganism onto a plate containing a solid nutrient source or growth medium. Such a technique is generally referred to as plating. By total viable count we mean the total number of bacteria capable of yielding a population discernible by the observer. Typically this will mean a visible colony on the surface of a growth medium such as nutrient agar plate.

However, microorganisms such as *Legionella pneumophila* in the environment may be subject to one or more stresses which prevent the microorganism from growing and multiplying in its environmental situation. Such stressed microorganisms would not divide at all or form a visible colony under normal culturing conditions. In the environment a proportion of microorganisms cells will generally be stressed due to environmental conditions, such as starvation, presence of biocide, heat shock and desiccation. Furthermore, these cells may be in a vulnerable physiological state in which the technique of plating the microorganisms may exacerbate stressing of those already stressed microorganisms cells due to the presence of atmospheric oxygen. Furthermore this could lead to artifactual death of the stressed bacteria leading to an underestimation of the total viable count.

In addition, underestimation of viable *Legionella pneumophila* with plating method might become hazardous in regard to its pathogenicity.

Since the 1970s it has been reported that scavengers of reactive oxygen species (ROS) should be used to limit the effect of oxidative stress during the plating process. This was reported by Speck et al, repair and enumeration of injured coliforms by a plating procedure, Appl Microbiol 29, 549-50 (1975); Martin et al Catalase: its effect on microbial enumeration. Appl Environ Microbiol 32, 731-4 (1976); Brewer et al Beneficial effects of catalase or pyruvate in a most-probable-number technique for the detection of *Staphylococcus aureus*. Appl Environ Microbiol 34, 797-800 (1977); McDonald et al, Enhanced recovery of injured *Escherichia coli* by compounds that degrade hydrogen peroxide or block its formation. Appl Environ Microbiol 45, 360-5 (1983); Marthi et al) Resuscitation effects of catalase on airborne bacteria. Appl Environ Microbiol 57, 2775-6 (1991); Busch and Donnelly Development of a repair-enrichment broth for resuscitation of heat-injured *Listeria monocytogenes* and *Listeria innocua*. Appl Environ Microbiol 58, 14-20 (1992); and Dukan et al, Oxidative stress defense and deterioration of growth-arrested *Escherichia coli* cells. J Biol Chem 274, 26027-32 (1999).

However, in all the aforementioned cases the inventors of the present invention believe that the ROS would be reduced by a direct route in which the compound reacts chemically with ROS.

Bérubé et al, "Rapid detection and identification of *Legionella pneumophila* by membrane immunoassay", Applied and Environmental Microbiology, 1989, 55, 1640-1641 describes the detection and identification of *Legionella pneumophila* by an immunoblot assay using a monoclonal antibody. No means is provided for dealing with the problem of injured bacteria.

An article by Pine et al (Role of keto acids and reduced-oxygen-scavenging enzymes in the growth of *Legionella* species. J Clin Microbiol 23, 33-42 (1986)) describes the necessity for the addition of keto acids and reduced oxygen scavenging enzyme is to optimise the growth of *Legionella pneumophila* and suggested using these materials in the medium used for standard enumeration of this microorganism.

However the use of keto acids and reduced oxygen scavenging enzyme alone is insufficient to repair the stressed *Legionella pneumophila* cells to be repaired and allow accurate enumeration. This is especially so when using a specific growth medium for *Legionella pneumophila*, such as buffered charcoal yeast extract (BCYE) agar medium. In fact, there is no data available concerning the optimisation of a standard medium useful for the accurate enumeration of *Legionella pneumophila*.

Thus an objective of the present invention is to find a method for accurately enumerating *Legionella pneumophila*. This is especially so in regard to its standard method using the plating technique.

SUMMARY OF THE INVENTION

Thus according to the present invention we provide a method for detecting and enumerating viable microorganisms in a sample suspected of containing said microorganisms (1) contacting said microorganisms of said sample with at least one repair compound and a growth medium, and
(2) incubating the product of steps (1), and
(3) detecting and quantifying said viable microorganisms, in which the microorganisms are of the species *Legionella pneumophila*, and in which the repair compound directly or indirectly causes an effect on the metabolism to reduce the oxidative stress of the microorganism.

By oxidative stress we mean an imbalance between the concentration of ROS (endogene production or exogene adduction) and the ability of the microorganisms to readily detoxify the reactive intermediates or efficiently repair the resulting damage. Such disruption of the normal metabolic processes of the microorganism can cause toxic effects due to the formation of free radicals and oxidising agents, such as peroxides, which may lead to damage to the components of the microorganisms cells, for instance DNA, proteins or lipids.

Causing an effect on the metabolism of the microorganism means bringing about changes to natural internal chemical processes within the microorganism cell.

Reference to endogenously means changes are brought about within the microorganism cell to reduce oxidative stress. This could for instance be changes to the metabolic processes within the microorganism. It may also include removal of ROS within the microorganism cell.

Desirably the repair compound may be or include at least one compound that inhibits the formation of and/or degrades ROS. In general this would be achieved by modification of the metabolism.

However, the repair compound may be or include at least one compound that indirectly inhibits the formation of and/or degrades the ROS. Such a compound that exerts an indirect effect on the ROS may do this by interfering with the metabolism of the microorganism. Such a compound may be regarded as indirectly reducing ROS endogenously for instance during aerobic respiration.

We have found that the present method induces the repair of stressed *Legionella pneumophila* cells and thus more accurately provides a total viable count. Unexpectedly we have also found that the method reduces the amount of incubation time required. In general we find that the method can reduce the incubation time by several hours and in some cases at least one day. In some cases method of the present invention may reduce the incubation time by up to several days, e.g. up to five days, by comparison to the conventional method.

Unexpectedly we have also found that the inventive method can bring about a reduction of interfering microorganisms i.e. those microorganisms other than the *Legionella pneumophila*.

DETAILED DESCRIPTION OF THE INVENTION

The method of the present invention desirably involves contacting stressed *Legionella pneumophila* microorganism cells with at least one compound that inhibits the formation of and/or reduces and/or removes ROS and this tends to induce repair of the stressed cells.

The *Legionella pneumophila* microorganism may be brought directly in contact with the repair compound upon collection of the sample. Thus the container into which the sample of water, believed to contain the microorganism, is collected may already contain the repair compound. Alternatively once a sample of water containing the *Legionella pneumophila* has been collected it may be diluted with dilution water containing repair compound for analysis purpose. In a further alternative the sample, optionally having been diluted, may be brought into contact with the growth medium containing the repair compound or the repair compound may be applied after contacting the microorganism with the growth medium.

One form of this invention desirably involves contacting said sample with a repair medium, preferably a non-selective repair medium, containing said repair compound and then bringing this into contact with a growth medium, preferably a selective growth medium. Preferably the repair medium is a liquid and more preferably a broth. Where the repair medium is a liquid this is suitably referred to as a liquid repair method. Typically in a liquid repair method the sample is first introduced into a liquid medium containing the repair compound. Ideally the liquid repair method allows stressed bacteria to repair in a non-selective liquid medium. Preferably the liquid repair method will employ a broth as the liquid medium. In general the liquid medium containing the microorganisms will then be transferred to a growth medium. The stressed microorganisms would either have been repaired prior to transference to the growth medium or would repair upon contact with the growth medium. More preferably the growth medium is a selective growth medium. Typically the liquid medium containing the microorganisms will be plated onto a selective growth medium plate such as a selective agar growth medium plate.

In an alternative preferred form step (1) comprises contacting said sample with a growth medium, preferably a non-selective growth medium containing said repair compound, and then bringing this into contact with a repair medium also containing said repair compound. Preferably the repair medium is a non-selective repair medium, more preferably a solid, and particularly preferably a selective agar growth medium. When the repair medium is a solid this is would be termed a solid repair method. Typically the solid repair method will involve contacting the sample with a non-selective growth medium containing of the repair compound. Subsequently this can be brought into contact with a selective growth medium containing the repair compound. In this form the selective ingredients and the compound or compounds, which prevents the formation, reduces or removes the ROS, will defuse across into the non-selective medium. Desirably the non-selective growth medium can be a non-selective agar growth medium. Suitably in this form the sample can be plated onto any non-selective agar and then a selective agar growth medium containing the compound or compounds that prevent the formation, reduces or removes the ROS is overlaid onto the non-selective agar growth medium.

In a further alternative form the sample may be applied to a selective growth medium which already contains the repair compound. Such a selective growth medium may be a selective agar growth medium. Plating of the sample may be carried out as described previously.

In a further alternative form the sample may be collected from water in the form of an aerosol. Typically the aerosol may be located in a cooling tower or air conditioner. Desirably the water condensed from the aerosol before testing according to the method of the present invention. In an alternative preferred form step (1) comprises contacting said sample from aerosol with a dilution water containing a repair medium, preferably a non-selective repair medium containing said repair compound, and then bringing this into contact with a growth medium also containing said repair compound.

In all of the aforementioned forms of the invention the growth medium should be suitable for growth of *Legionella pneumophila*. Suitable growth medium types are documented in the literature and are well known to the skilled person. Normally the growth medium should contain activated carbon and cysteine.

It is preferred that the selective growth medium is a selective agar growth medium and more preferably is a buffered charcoal yeast extract (BCYE) agar growth medium. The BCYE growth medium would become selective by the addition of antibiotic supplement. A highly desirable BCYE growth medium with antibiotic is known as GVPC (Glycine, Vancomycine, Polymyxine B, Cycloheximide).

The plating method is documented in the literature and is well known that the skilled person. Typically the method will involve applying a quantity of these samples of water onto agar gel that has been placed in a Petri dish. This may be termed a Petri dish method or an agar plating method. The aim of the agar plating is to spread an aliquot, typically 100 μl of water suspected of containing the microorganism, termed a bacterial suspension, onto a solid medium in a Petri dish. Glass beads or a cell scraper can be used to spread the bacterial suspension on the agar plate. After spreading, most of the liquid is absorbed by the agar and a thin layer with bacteria remains on the agar surface. By incubation, bacterial growth in the form of colonies developed on the agar surface. The incubation will occur at a temperature best suited for the microorganism, which is well documented in the literature and known to the skilled person. Typically the temperature will be between 30° C. and 50° C., for instance around 37° C.

The repair compound should be added in an amount effective to reduce oxidative stress of the microorganism. Preferably this will be an amount effective to reduce or substantially remove ROS in the microorganism cell.

In one preferred form of the invention the repair compound includes at least thioglycolic acid or its salts thereof. Desirably the thioglycolic acid is in the form of thioglycolate and usually in the form of the sodium salt. The thioglycolic acid or salts scavenge exogenously ROS. Preferably the amount of thioglycolic acid or salts of present in a medium at a concentration of between 0.01 and 1% by weight (calculated as thioglycolate).

In another preferred form of the invention the repair compound includes at least one compound selected from the group consisting of catalase, ascorbic acid (or salt thereof), metabisulphurous acid (or salt thereof), dimethyl sulphoxide (DMSO), 3,3'-thiodipropionic acid (TDPA) (or salt thereof) and pyruvic acid (or salt thereof). These compounds have all been found to reduce or remove ROS. When ascorbic acid and pyruvic acid are used they are preferably present in a medium at a concentration of between 0.01 and 1% by weight calculated as the sodium salt. DMSO is preferably used at a concentration between 0.01 and 0.1% by weight and catalase is desirably present at a concentration in the range of 0.001 to 0.1% by weight. Pyruvic acid, especially sodium pyruvate, is particularly preferred.

In a more preferred form of the invention the repair medium or growth medium will comprise both thioglycolic acid (or salt) and at least one of the group selected from catalase, ascorbic acid (or salt thereof), metabisulphurous acid (or salt thereof), dimethyl sulphoxide (DMSO), 3,3'-thiodipropionic acid (TDPA) (or salt thereof) and pyruvic acid (or salt thereof). The combination of thioglycolate and sodium pyruvate is especially preferred.

In the case where the repair compound may be or include at least one compound that indirectly inhibits the formation of and/or degrades the ROS, said compound may bring about reduced levels of ROS by interfering with the metabolism of the microorganism. Typically such compounds will include amino acids or their salts. A particularly preferred compound is glutamic acid or glutamate salt.

In a still further preferred form of the invention the repair compound would include glutamic acid or glutamate salt, especially the sodium salt. In general the amount of glutamic acid or glutamate will be between 0.01 and 5% by weight calculated as the sodium salt.

It is particularly preferred that the repair compound will include both pyruvic acid or pyruvate (especially the sodium salt) together with glutamic acid or glutamate (especially as the sodium salt). This combination of pyruvic acid or pyruvate with glutamic acid or glutamate seems to induce a synergistic effect in that it allows a higher estimation (and therefore more accurate estimation) of culturable *Legionella* than either compound respectively used alone. Furthermore we have found that this combination brings about a further reduction of lag phase during development of the *Legionella pneumophila*, in particular in a liquid medium. Such a reduction of lag phase in liquid medium results in a reduction of the time required to obtain a visible colony on agar plate.

Desirably the amount of pyruvate and glutamate will be as stated previously. It is particularly preferred that the ratio of glutamate to pyruvate will be in the range between 1:1 and 50:1, especially between 5:1 and 20:1 and more especially between 7:1 and 15:1.

Glutamate is not known to be an antioxidant. However, it s appear that indirectly glutamate could reduce the endogenous production of ROS naturally formed during growth or their consequences on macromolecules (oxidation).

Without being limited to theory, it thought that the glutamic acid changes the metabolism of *Legionella* to increase the effect of pyruvate and that this interference with the metabolism of *Legionella* indirectly inhibits the formation of and/or degrades intracellular ROS.

It may also be desirable to include a keto acid and/or a reduced oxygen scavenging enzyme with the repair medium and/or growth medium. A keto acid and/or a reduced oxygen scavenging enzyme are not considered a repair compound according to the present invention. Nevertheless, it may be beneficial to include one or both of these compounds with any of the aforementioned repair compounds or combinations thereof.

Detecting and quantifying the viable microorganisms can be carried out by any of the known technique is documented in the literature. Typically this will mean counting the visible colonies of the surface of the growth medium, such as nutrient agar plate.

The method according to present invention facilitates the accurate quantitative determination for the existence of *Legionella pneumophila*. Furthermore the incubation time may be significantly reduced. The method is suitable for detecting *Legionella pneumophila* in samples derived from any of the group selected from industrial cooling waters, drinking waters, and natural waters.

The present invention also incorporates a kit for more accurately detecting and enumerating viable microorganisms of the species *Legionella pneumophila* in a sample suspected of containing said microorganisms comprising:
(1) at least one repair compound,
(2) a growth medium,
(3) a means for incubation
(4) a means for detecting and quantifying the microorganisms,
in which the repair compound directly or indirectly causes an effect on the metabolism to reduce oxidative stress of the microorganism.
in which the microorganisms are of the species *Legionella pneumophila*, and in which the repair compound directly or indirectly causes an effect on the metabolism to reduce the oxidative stress of the microorganism.

The kit may also contain any of the embodiments described in regard to the first aspect of the invention.

The kit is suitable for use with the method of the present invention and enables more accurate enumeration of *Legionella pneumophila*.

The following examples illustrate the invention.

EXAMPLE 1

A suspension of *Legionella pneumophila* was added to 5 flasks containing 50 ml of sterile phosphate buffer (PBS) at final concentration of $10^8$ bacteria/ml. A biocide solution was added to obtain final concentrations in the range 10 to 30 mg/L. One flask was performed in parallel and served as control without biocide. The biocide used is a THPS (tetrakis (hydroxymethyl)phosphonium sulfate).

After homogenization, all suspensions were incubated at 37±1° C., in the dark and with agitation for 60 min. Biocide is eliminated by 2 washes in PBS (5,000×g, 10 min) before bacterial counting. Serial dilution is done and 2 aliquot of 100 μl from the same dilution is plated on BCYE agar plate and BCYE supplemented with 0.1% of pyruvate.

Figure 1:
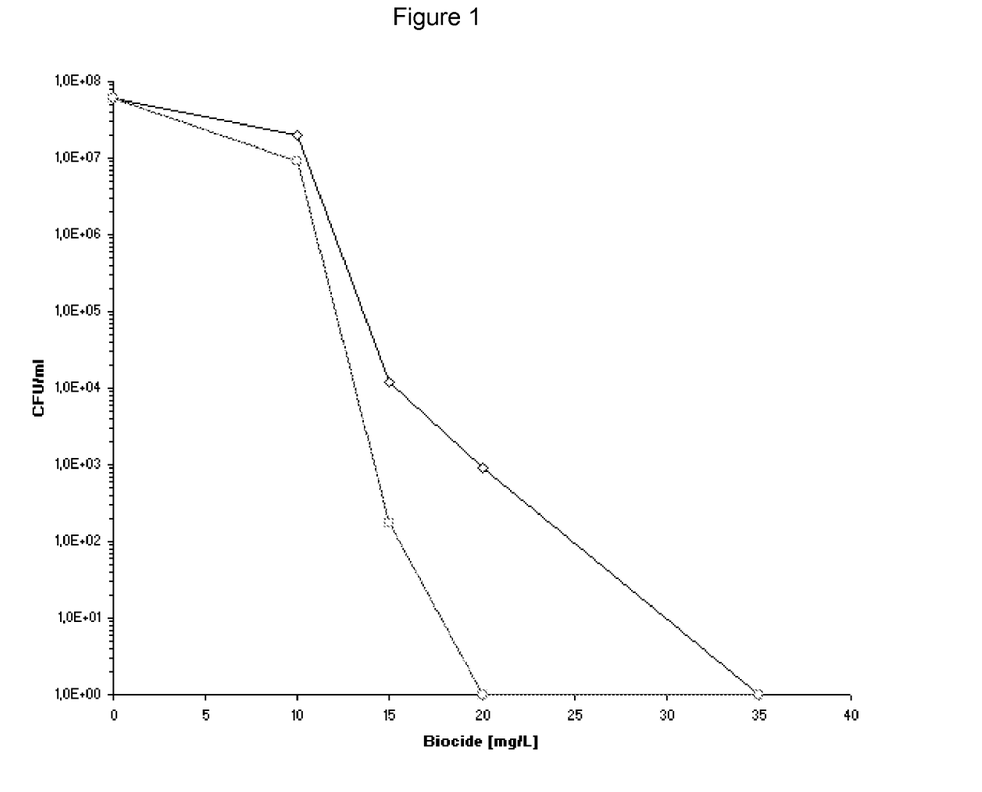
FIG. 1 is a graph showing the culturable *Legionella Pneumophila* enumerated after biocide treatment on standard BYCE medium and supplemented BCYE, according to the method of Example 1.

The results are shown in FIG. 1. FIG. 1 shows the enumeration of culturable *Legionella Pneumophila* after biocide treatment on BCYE medium (squares) and BCYE medium plus 0.1% pyruvate (diamonds). The presence of the biocide is to introduce stressing of the microorganism. The results show that in the presence of pyruvate a much higher microorganism count is achieved where the microorganisms are stressed. In the absence of biocide the microorganisms are unstressed. In this case it can be seen that the presence and absence of pyruvate give the same result. This demonstrates that the presence of the pyruvate stressed microorganisms of *Legionella pneumophila* are repaired and thus a more accurate reading is provided.

EXAMPLE 2

A suspension of *Legionella pneumophila* was added to 1 flask containing 50 ml of sterile phosphate buffer (PBS) at final concentration of $10^8$ bacteria/ml. A biocide solution was added to obtain final concentration of 15 mg/L. The biocide used is a THPS (tetrakis(hydroxymethyl)phosphonium sulfate).

Figure 2:
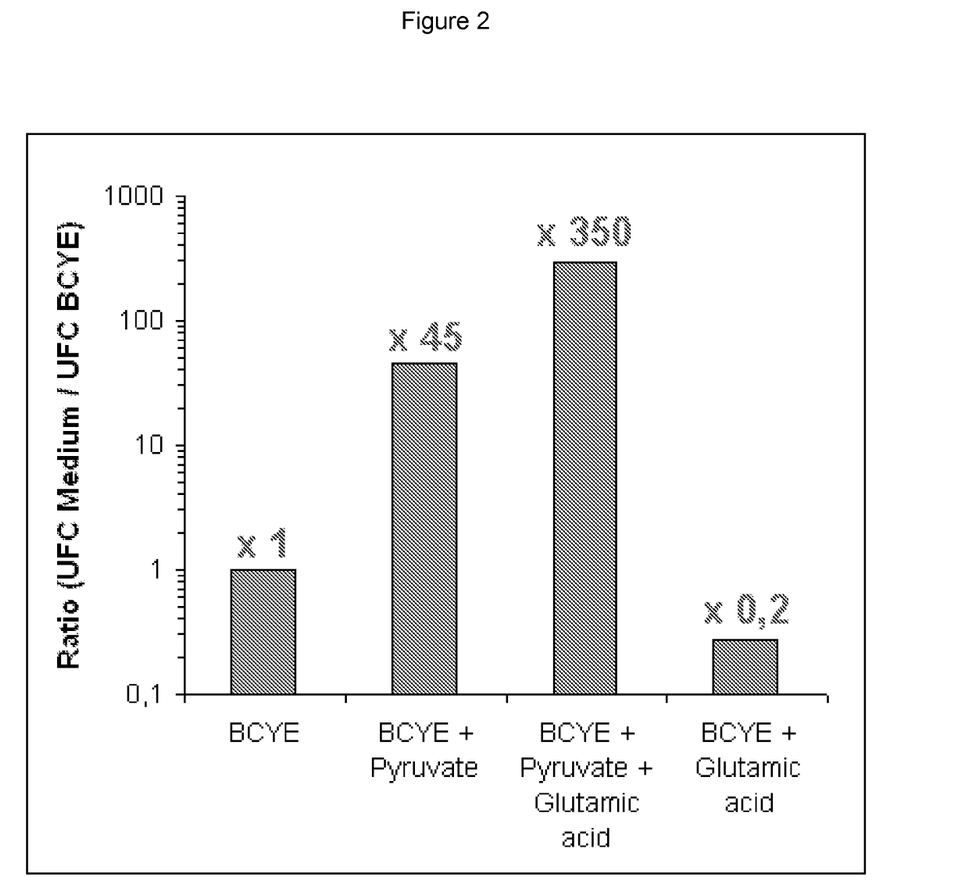
FIG. 2 is a chart showing the ratio between number of culturable *Legionella* obtained on standard BYCE medium and on supplemented BYCE, according to the method of Example 2.

After homogenization, suspension was incubated at 37±1° C., in the dark and with agitation for 60 min. Biocide is eliminated by 2 washes in PBS (5,000×g, 10 min) before bacterial counting. Serial dilution is done and 2 aliquot of 100 μl from the same dilution is plated on BCYE agar plate, BCYE supplemented with 0.1% of pyruvate, BCYE supplemented with 0.1% of pyruvate and 1% of glutamic acid and BCYE supplemented with 1% of glutamic acid. The results are shown in FIG. 2. FIG. 2 shows the ratio between number of culturable *Legionella* obtained on standard medium (BCYE) and number of culturable *Legionella* obtained on medium supplemented with 2 compounds described in this patent (Pyruvate & Glutamic acid).

Addition of pyruvate in the standard medium (BCYE) leads to an increase of culturable *Legionella* detected after biocide treatment (number of culturable *Legionella* on "BCYE+Pyruvate" is 45 times higher than number of culturable *Legionella* standard medium). Addition of glutamic acid alone in the standard medium (BCYE) leads to a decrease of culturable *Legionella* detected after biocide treatment (×0.2). Surprisingly, addition of pyruvate and glutamic acid lead to an increase of culturable *Legionella*, with a larger number than that observed with compounds alone. This demonstrates that the presence of the pyruvate stressed microorganisms of *Legionella pneumophila* are more repaired with addition of glutamic acid and thus a more accurate reading is provided.

EXAMPLE 3

Figure 3:
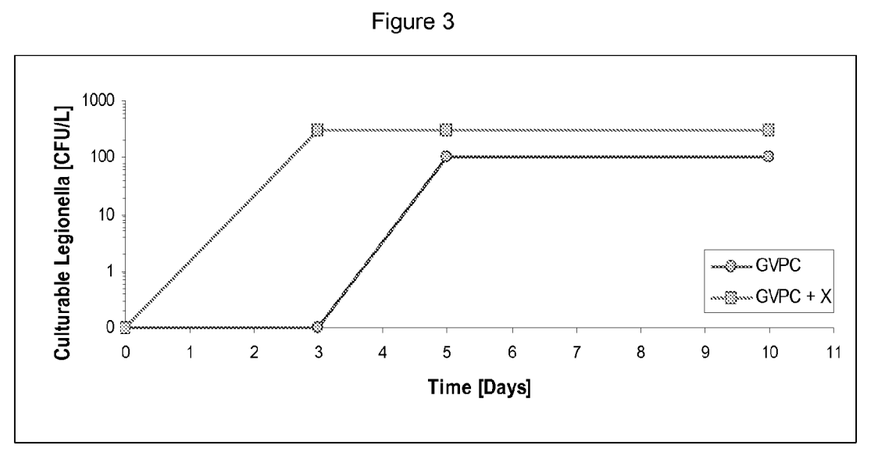
FIG. 3 is a graph showing the culturable *Legionella Pneumophila* enumerated over time on GVPC medium and supplemented GVPC (GVPC + X), according to the method of Example 3.

A suspension of *Legionella pneumophila* was added to 1 flask containing 1 L of sterile phosphate buffer (PBS) at final concentration of $3 \times 10^2$ bacteria/L. After concentration by filtration, 2 aliquot of 100 µl from the same suspension is plated on GVPC agar plate (GVPC), GVPC supplemented with 0.1% of pyruvate and 1% of glutamic acid (GVPC+X). Numbers of colony were counted at 0, 3, 5 and 10 days after incubation at 37° C. The results are shown in FIG. 3. At 3 days of incubation, no colony was visible on GVPC medium when 300 colonies could be already enumerated on GVPC supplemented medium. At 5 and 10 days of incubation, 100 colonies could be enumerated on GVPC where 300 colonies could be enumerated on GVPC supplemented medium. By using supplemented medium, colonies could be detected at least 2 days before that enumerated on standard GVPC.

EXAMPLE 4

Figure 4:
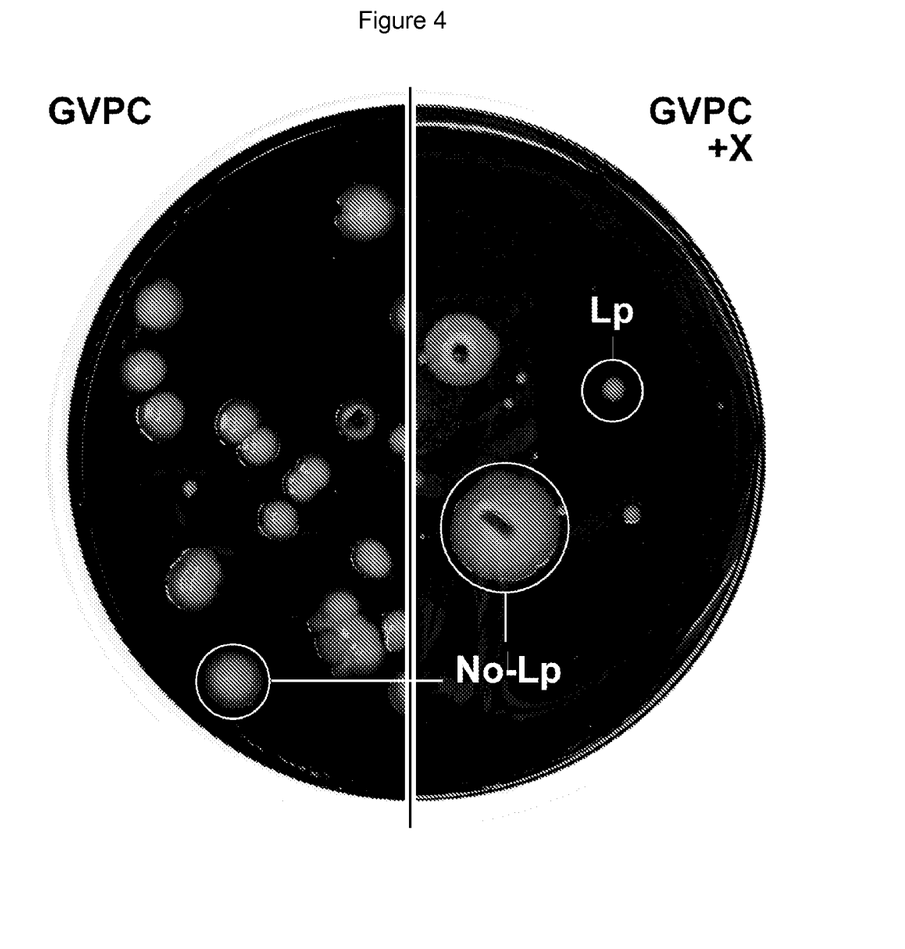
FIG. 4 is an image showing the colonies of not-*Legionella Pneumophila* (No-LP) and colonies of *Legionella Pneumophila* enumerated on GVPC medium and supplemented GVPC (GVPC + X), according to the method of Example 4.

An environmental sample containing culturable *Legionella* was concentrate by filtration. From concentrate, 2 aliquot of 100 µl from the same suspension is plated on GVPC agar plate (GVPC), GVPC supplemented with 0.1% of pyruvate and 1% of glutamic acid (GVPC+X). Numbers of colony were counted 5 days after incubation at 37° C. In this case, no *Legionella* colonies could be enumerated on standard medium (GVPC), where 17 colonies of Not-*Legionella* colonies could be enumerated. By contrast, at least 10 *Legionella* colonies could be enumerated on Supplemented medium (GVPC+X), where only 2 colonies of Not-*Legionella* colonies. This is shown in FIG. 4.

EXAMPLE 5

A suspension of *Legionella pneumophila* was added to 1 flask containing 50 ml of sterile phosphate buffer (PBS) at final concentration of $10^8$ bacteria/ml. A biocide solution was added to obtain final concentration of 15 mg/l. The biocide used is a THPS (tetrakis(hydroxymethyl)phosphonium sulfate).

Figure 5:
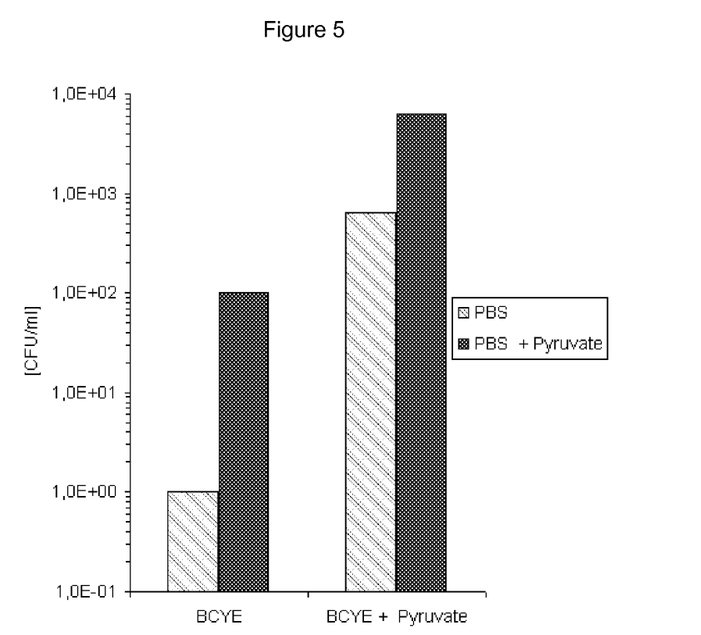
FIG. 5 is a chart showing the number of culturable *Legionella pneumophila* obtained on standard BYCE medium and supplemented BYCE after dilution in PBS or PBS+Pyruvate, according to the method of Example 5.

After homogenization, suspension was incubated at 37±1° C., in the dark and with agitation for 60 min. Biocide is eliminated by 2 washes in PBS (5,000×g: 10 min) before bacterial counting. Serial dilution is done either in PBS or PBS supplemented with 0.5% of pyruvate. From each dilution buffer (with or without pyruvate addition), 2 aliquot of 100 µl from the same dilution is plated on BCYE agar plate, BCYE supplemented with 0.1% of pyruvate. The results are shown in FIG. 5. FIG. 5 shows the number of culturable *Legionella pneumophila* obtained on standard medium (BCYE) and number of culturable *Legionella pneumophila* obtained on standard medium supplemented with pyruvate after dilution in PBS (scratched bar) or PBS+Pyruvate (dark bar).

As already observed, addition of pyruvate in the standard medium (BCYE) leads to an increase of culturable *Legionella pneumophila* detected after biocide treatment, when PBS only are used to dilute solution. Surprisingly, addition of pyruvate in the dilution buffer leads to an increase of culturable *Legionella pneumophila* detected on standard medium (BCYE), but also on standard medium supplemented with pyruvate. This demonstrates that the presence of the pyruvate in dilution buffer allow a more repaired of stressed *L. pneumophila*.

The invention claimed is:

1. A method for detecting and enumerating viable microorganisms in a sample suspected of containing said microorganisms, the method comprising:
   (1) contacting said microorganisms of said sample with at least one repair compound and a growth medium, and
   (2) incubating the product of step (1), and
   (3) detecting and quantifying said viable microorganisms,
   in which the microorganisms are of the species *Legionella pneumophila*,
   in which the repair compound directly or indirectly causes an effect on the metabolism to reduce the oxidative stress of the microorganism,
   wherein the growth medium is a buffered charcoal yeast extract (BCYE) or glycine, vancomycine, polymyxine B, cycloheximide (GVPC) agar growth medium,
   wherein the repair compound is a mixture of pyruvic acid or a salt thereof and glutamic acid or a salt thereof and
   wherein the ratio of glutamic acid or a salt thereof and pyruvic acid or a salt thereof is in the range between 1:1 and 50:1.

2. A method according to claim 1 in which step (1) comprises contacting said sample with a repair medium containing said repair compound and then bringing this into contact with a growth medium.

3. A method according to claim 2 in which the repair medium is a liquid.

4. A method according to claim 1 in which step (1) comprises contacting said sample with a growth medium and then bringing this into contact with a repair medium containing said repair compound.

5. A method according to claim 4 in which the repair medium is a selective repair medium.

6. A method according to claim 1 in which step (1) comprises contacting said sample with the growth medium containing said repair compound.

* * * * *